United States Patent [19]

Knifton

[11] 3,981,916

[45] Sept. 21, 1976

[54] REDUCTION OF NITROPARAFFIN SUBSTRATES TO THEIR CORRESPONDING OXIMES USING A SILVER SALT CATALYST

[75] Inventor: John F. Knifton, Poughquag, N.Y.

[73] Assignee: Texaco Inc., New York, N.Y.

[22] Filed: July 9, 1970

[21] Appl. No.: 53,702

[52] U.S. Cl. .............................................. 260/566 A
[51] Int. Cl.$^2$ ...................................... C07C 131/04
[58] Field of Search ....................... 260/566 A, 566

[56] References Cited
UNITED STATES PATENTS

| | | | |
|---|---|---|---|
| 2,711,427 | 6/1955 | Christian | 260/566 A |
| 2,820,826 | 1/1958 | Temin et al. | 260/566 A |
| 2,945,065 | 7/1960 | Donaruma | 260/566 A |
| 3,354,212 | 11/1967 | Donaruma | 260/566 A |
| 3,428,625 | 2/1969 | Strauss | 260/566 A |

*Primary Examiner*—Gerald A. Schwartz
*Attorney, Agent, or Firm*—T. H. Whaley; C. G. Ries; Bernard Marlowe

[57] ABSTRACT

This invention concerns the reduction of nitroparaffin substrates to the corresponding oxime in a carbon monoxide atmosphere under moderate reaction conditions using silver salt catalysts solubilized in nitrogenous base.

11 Claims, No Drawings

REDUCTION OF NITROPARAFFIN SUBSTRATES TO THEIR CORRESPONDING OXIMES USING A SILVER SALT CATALYST

This invention concerns the partial reduction of nitroparaffin substrates to the corresponding oxime in good yield and substantially free from amine contaminants.

More particularly, this invention concerns the use of silver salts to effect the substantially quantitative reduction of nitroparaffin substrates to the oxime under moderate reaction conditions.

Oximes are valuable starting materials in organic synthesis as well as being useful in themselves. For example, oximes react with hydrogen cyanide to form hydroxyaminonitriles, undergo the Beckmann rearrangement and can be acylated and alkoxylated to useful products.

Numerous preparative procedures have been utilized to produce oximes, particularly paraffinone oximes. Most commonly, the paraffinone oximes have been prepared by the base catalyzed reaction of aliphatic ketones with hydroxylamine salts. Unfortunately, the reaction is reversible, and concurrently produces contaminants which are difficult to separate from the oxime product. Similarly, other less favored processes also have not been entirely satisfactory for one reason or another. For instance, many of the reductive processes result in the formation of substantial quantities of the fully reduced amine instead of the desired oxime product. Still other preparative techniques produce the oxime but the oxime is contaminated with difficulty separable impurities. Other processes require several steps, require tedious and time-consuming separations which ultimately result in poor yields.

With the advent of relatively large and inexpensive quantities of nitroparaffins from petrochemical sources, interest in reductive processes has been revived. Particularly sought are procedures which can be used to produce both cylic and linear oximes from the corresponding nitroparaffin substrates in good yield, relatively free from tenacious contaminants. In addition to good yield and freedom from contaminants, a useful reductive process would function at relatively moderate conditions of temperature and pressure and would be equally effective in reducing the neat nitroparaffins or the nitroparaffins accompanied by large quantities of paraffinic hydrocarbons. A further attribute sought would be that the process would be equally effective on highly purified specific nitroparaffins or on their purified mixtures.

Recently, the applicant developed a novel reductive process which represented a substantial improvement over reductive processes of the prior art. Ser. No. 807,943 filed Mar. 17, 1969 in the U.S. Patent Office.) The inventive process utilized a homogeneous aqueous catalyst system comprising critical proportions of copper salts, in a basic media provided by nitrogenous base and water under an atmosphere of carbon monoxide.

The instant invention represents an alternative process for effecting the selective reduction of nitroparaffins to the corresponding paraffinone oxime. The novel process also utilizes a homogeneous catalyst system in a carbon monoxide atmosphere, but unlike the filed process described supra, it employs silver salts as the catalytic cation. While the inventive process also employs critical proportions of nitrogenous base and silver salt, the reaction condition parameters such as temperature and pressure, are not only quite specific but are also quite distinct from those used when copper salts are the catalytic agent. Furthermore, although water is a preferred component of the catalyst system, its presence is not critical to operability.

Surprisingly, the reaction conditions which produced a highly active silver salt catalyst were found to be ineffective to activate similar types of metal ions such as mercury(II), cobalt(II), nickel(II) and manganese. Similarly, other catalytic metal cations such as iron, chromium and gold were also inactive under the reaction conditions in which the silver salts were active.

It is an object of this invention to provide an alternative method for producing paraffinone oximes from both linear and cyclic nitroparaffins in good yield, substantially free from the fully reduced paraffinic amines produced in the reductive processes of the prior art.

Another object of this invention is the development of the aforesaid selective reductive process capable of utilizing crude nitration mixtures as starting materials.

Another more specific object of this invention is to provide processes for reducing nitroparaffins containing 3 or more carbon atoms, in good yield, under moderate reaction conditions, to their corresponding oximes utilizing presently available techniques and process equipment.

An even more specific object of this invention is to provide a homogeneous catalyst system utilizing silver as the catalytic cation to reduce nitroparaffins to the corresponding paraffinone oxime.

Additional objects are the development of reduction processes employing an inexpensive, stable and long-lived catalyst system which gives optimum results under moderate conditions of pressure and temperature, utilizing process equipment and techniques presently employed in the art.

Further objects will suggest themselves to those skilled in the art of catalysis after a perusal of this disclosure.

In practice, the above objects are achieved by contacting nitroparaffins containing at least 3 carbon atoms and up to 40 carbon atoms and higher, with a catalyst system comprising at least one silver salt, water and nitrogenous base having a pKa of at least 9.0 (said silver salt and base being present in a critical ratio) in a carbon monoxide atmosphere to form a reaction mixture, and heating said reaction mixture between 40° and 120° C. at super atmospheric pressures, until the nitroparaffin substrates are reduced to the corresponding paraffinone oximes.

In the favored practice each molar equivalent of a nitroparaffin substrate selected from the group consisting of nitrocyclohexanes and linear nitroparaffins containing from about 10 to 20 carbon atoms is:
1. admixed with a catalyst system comprising:
    a. at least 0.01 molar equivalents of at least one silver salt,
    b. at least 0.1 molar equivalents of at least one water-miscible, nitrogenous base having a pKa of at least 9.0 and
    c. from about 0 to 100 molar equivalents of water to form a reaction mixture,
2. providing a carbon monoxide atmosphere for said reaction mixture,
3. heating said reaction mixture between about 40° and 120° C. at superatmospheric pressures ranging from about 50 psig to about 1000 psig, until substantial conversion of the nitrated paraffins to their paraffinone oximes is obtained, and 4. isolating the oxime produced therein.

In the preferred practice, each molar equivalent of a mono-nitroparaffin substrate selected from the group consisting of nitrocyclohexane, single linear nitroparaffins containing between 10 and 15 carbon atoms and mixtures of linear nitroparaffin containing from between 10 to 15 carbon atoms is:

1. admixed with a catalyst system comprising:
    a. from 0.1 to 2 molar equivalents of a silver salt,
    b. from 1 to 20 molar equivalents of water-miscible, nitrogenous base having a pKa between 9 and 11.5 selected from the group of bases consisting of bidentate and multidentate nitrogenous bases, and
    c. from about 0 to 10 molar equivalents of water to form a reaction mixture,
2. providing a carbon monoxide atmosphere for said reaction mixture,
3. heating said reaction mixture between about 70 and 90° C. at superatmospheric pressures ranging from about 300 psig to 1000 psig, until substantial conversion of the mono-nitrated paraffins to their paraffinone oxime are obtained, and
4. isolating the oxime produced therein.

In order to aid in the understanding of the inventive concept, the following additional disclosure is submitted:

A. Nitroparaffin Substrate — Any paraffinic substrate containing from 3 to 40 carbon atoms, or more, and at least one nitro group per molecule can be employed. The most useful substrates are the mono-nitro linear and cyclic nitroparaffins such as the nitrobutanes, nitropentanes, nitrohexanes, nitroheptanes, nitrooctanes, nitrononanes, nitrodecanes, nitrocundecanes, nitrododecanes, as well as their higher homologues. The favored substrates are mixtures of linear nitroparaffins containing from about 10 to 20 carbon atoms. The substrates can be in the form of pure or partially purified nitration mixtures derived from the vapor liquid phase nitration of paraffins or from other sources. The substrates can comprise single nitroparaffins or their mixtures, neat or containing inert solvents or diluents such as paraffins, ethers and the like. The preferred nitroparaffin substrates are nitrocyclohexanes and mixtures of linear nitroparaffins containing 10 to 15 carbon atoms. These substrates are preferred since they are readily available at low cost and they lend themselves to substantially complete conversions to the desired oxime within relatively short reaction times.

B. Inert Diluent — The novel reduction process proceeds most rapidly in the absence of inert diluent. However, it is frequently desirable to utilize the crude or partially purified nitration mixtures derived from the vapor-liquid phase nitration of n-paraffin streams as starting materials without stripping off the unreacted n-paraffins. Further, the presence of a water-immiscible diluent or solvent facilitates isolation of the oxime product by concentrating the product within the organic phase. For these reasons, inert diluents or solvents can be employed without adversely affecting the degree of conversion to the oxime. Broadly speaking, any liquid in which the nitroparaffin substrate is soluble, and which is inert to reduction under the conditions of the invention process, can be used as diluents. These include the alkyl ethers such as diethyl ether, dibutyl ether, aromatics such as benzene, toluene and xylene, as well as the aforementioned liquid paraffins. Where the nitroparaffins are reduced in the absence of diluents, one or more of these diluents can be subsequently added to extract the oxime product from the reaction mixture and facilitate purification. Particularly useful for this purpose are the dialkyl ethers.

C. Carbon Monoxide Atmosphere — Insofar as can be determined the best balance of high conversion to the oxime within a short reaction time without substantial formation of amine is obtained using a substantially carbon monoxide gaseous atmosphere. Nitrogen or inert gases such as helium or argon are unsatisfactory, while reductions conducted in mixtures of carbon monoxide with helium, argon or nitrogen diluents are undesirably slow and offer no concurrent advantage.

Ordinarily the carbon monoxide is sparged into the reactor after all of the liquid components of the reaction mixture have been added and mixed. Then the air is flushed out of the system and the reaction mixture is heated in the carbon monoxide atmosphere until the desired reduction takes place.

D. Temperature — The reaction temperature used in the reaction is critical in at least two respects. Below about 40°C the rate of reduction is too slow to be measured while above 120°C, where the catalytic activity is rapid, substantial catalyst deactivation takes place and catalyst life is substantially diminished. Inasmuch as temperatures of 70° to about 90°F give a reasonable balance of catalyst life with fairly fast reductions, these represent the favored range of temperature, particularly under the preferred CO pressure conditions.

E. Pressure — Superatmospheric reactor pressures from about 50 psig to 1000 psig and higher are required to obtain reasonable rates of reduction. Pressures from about 300 psig to 1000 psig coupled with reaction temperatures of 70° to 90°C consistently give the best conversions and are therefore preferred.

F. Reaction Times — The reactor time required for substantial production of the oximes is a variable, dependent primarily upon the temperature and pressure employed, the particular nitroparaffin substrate to be reduced, the basicity of the nitrogenous base and the quantity of inert diluent. To a lesser extent it is dependent on the size of the batch. Under most circumstances, when from 75 to 90% by weight ethylenediamine is used in conjunction with 5 to 10% by weight of silver salt, the reduction of the nitroparaffin is ordinarily complete within eight hours. Di- and higher nitrated paraffins may require longer reaction times.

G. Catalyst System — The catalyst system comprises the silver salt component, the nitrogenous base component used to provide the required basicity and solubilization of the silver salt and in most cases water to also promote solubilization of the silver salts and the presence of hydroxy ions. The parameters of the catalyst system based upon the reduction of a linear mononitroparaffin substrate, appears below. Di-, tri- and higher nitreated substrates may require somewhat larger quantities of the various components of the catalyst system.

1. Silver Salt — As indicated earlier, silver salts, which are soluble in solutions of nitrogenous bases, can be employed as the cationic catalyst component. These include the silver salts of mineral acids such as silver nitrate and the salts of organic acids such as the mono, di and polycarboxylic acids such as silver acetate, silver formate, silver tartrate, and silver citrate. Silver acetate and silver nitrate are the preferred silver salts because they consistently produce good conversions.

The concentration of silver salts employed may range upward from about 0.01 mole for each mole of the nitroparaffin substrate employed. The preferred ratio of silver salt catalyst to nitroparaffin varies from 0.1 to 2 moles of silver catalyst for each mole of nitroparaffin present.

2. Nitrogenous Base — The nitrogenous bases which function well in the invention process are ordinarily those aliphatic primary or secondary amines which are miscible with water and which are capable of solubilizing or chelating the catalytic silver cation. These bases must have pKa base strengths greater than 9.0 (when measured at 25° – 30°C, in at least a 0.1 molar aqueous metal salt solution) to be effective. It is thought, without limiting the invention thereby, that this basicity may be necessary to insure the formation of the more reactive nitroparaffin anion. Bidentate and multidentate amines such as ethylenediamine, triethylenetetramine, tetraethylenepentamine, 3,3$^1$-iminobispropylamine and 1,6-hexanediamine all give consistently good results (as can be seen from Table I) and are therefore preferred. Other monodentate amines such as n-hexylamine, n-butylamine and having the requisite pKa are less favored since they produce a mixture of products including small quantities of the desired oximes. Pyridine, N,N,N$^1$N$^1$-tetramethylenediamine, morpholine and triethanolamine fail to produce oxime product, presumably because of their low pKa.

Although the role of the nitrogenous base in the reduction process is not certain, it has been found that at least 0.1 mole of nitrogenous base should be used for each mole of nitroparaffin substrate charged. To obtain the best balance of optimum yields in the shortest possible reaction time it is preferable that from 1 to 20 moles of base be present for each mole of nitroparaffin present.

3. Water Concentration — The presence of small quantities of water in the reaction mixture is preferable. While no mechanism is relied on, it appears plausible that the water is the source of hydroxyl ion used in the reduction. However, if too much water is present it acts as a diluent for the nitrogenous base, thereby lowering the pH of the solution so that reduction to oxime either does not take place at all or the rate or extent of reduction is substantially retarded. For this reason a ratio of from 0 to 100 moles of water for each mole of nitrogenous base is required for satisfactory results with 0 to 10 moles of water preferred.

H. Experimental Procedure — The reductive process is ordinarily performed as follows:

A conveniently sized reactor fitted with gas inlet, condenser, stirring, heating and pressurizing means, is charged with nitroparaffin substrate, and the three components of the catalyst system, that is, the silver salt, the nitrogenous base and water.

Carbond monoxide is then passed into the reactor to saturate the catalyst solution and provide a reducing atmosphere. The resulting reaction mixture is heated between about 40° and 120°C, preferably from about 70° to 90°C, at pressures of CO ranging from about 50 psig to 1000 psig or higher, until the desired oxime product is produced. If inert diluent is present the oxime is concentrated in the organic phase, if no inert diluent is employed the reaction mixture is extracted with solvents such as ethers or aromatics (benzene, toluene, xylene and the like) to separate the oxime. In either event, the extract of product in the organic solvent is washed several times with water, then vacuum distilled to produce the oxime product. Elemental analysis, infra-red gas chromatography and nuclear magnetic resonance spectra are used to establish that the desired oxime product has been prepared.

Having described the inventive process in general terms, the following examples are submitted to supply specific illustrative embodiments:

EXAMPLE 1

Preparation of $C_{10}$–$C_{14}$ Mixture of Oximes from a $C_{10}$–$C_{14}$ Nitroparaffin-Paraffin Mixture To a suitable autoclave-type reactor provided with pressurizing, heating, cooling, agitating and distillation means is added a one part-by-weight portion of a charge stock comprising 15 parts by weight of $C_{10}$–$C_{14}$ mixture of nitroparaffins (0.56 molar concentration), 82 parts by weight of $C_{10}$–$C_{14}$ paraffin (3.8 molar concentration) and 3 parts by weight of other oxygenates, produced by the vapor-liquid phase nitration of $C_{10}$–$C_{14}$ mixture of paraffins with $NO_2$. Also added to the reactor is one part-by-weight portion of catalyst solution composed of 5 parts by weight of silver acetate (0.26 molar concentration), 87 parts by weight of ethylenediamine (13 molar concentration) and 8 parts by weight of water (4 molar concentration). The molar ratio of silver acetate to nitroparaffin is about 1:2. The mixture is pressurized to 500 psig with carbon monoxide, sealed, and agitated, while heating to 85°C for about 6 hours. On cooling and degassing, the product mixture is removed, allowed to cool to room temperature and extracted 3 times with a 0.5 parts by weight portion of diethylether. The pooled ethereal extracts are water washed and vacuum distilled under 2 mm of mercury pressure to produce a reddish-yellow liquid residue. Infrared and nuclear magnetic resonance spectral techniques and authenticated samples of the oximes confirm this residue to be the expected $C_{10}$–$C_{14}$ mixture of paraffin oximes. The conversion of nitroparaffin is 73% of theory and the yield of $C_{10}$–$C_{14}$ paraffinic oximes obtained is 78% of theory.

EXAMPLE 2

Reduction of Cyclohexanone Oxime from Nitrocyclohexane.

Using the same general reduction procedure, isolation and purification techniques described in Example 1, a catalyst solution comprising 5 parts by weight of silver acetate (0.26 molar concentration, 0.1 moles), 87 parts by weight of ethylenediamine (13 molar concentration) and 8 parts by weight of water (4.0 molar concentration) is stirred rapidly, and 0.2 mole of nitrocyclohexane is added. The solution mixture is pressurized to 500 psig of carbon monoxide and heated to 85°C. The conversion of nitrocyclohexane to the oxime is complete within 5 hours. On cooling, the reaction mixture containing product is cooled, evaporated under reduced pressure to about 50% of its volume, treated with an equal weight of water and extracted 3 times with 1 part by weight of diethylether. Evaporation of the combined ethereal extracts (under reduced pressure) produces a yellow-colored solid, which upon recrystallization from 50:50 water ethanol mixture produces a white crystalline product. Confirmation and identification of the product as cyclohexane oxime, is accomplished using elemental analyses, infrared and nuclear magnetic resonance techniques. A conversion of 100% of nitrocyclohexane is obtained and the yield of cyclohexanone product is 63%, based on theory. The cyclohexanone is of sufficient purity to be converted quantitatively by acid hydrolysis to caprolactam, an intermediate in the preparation of polyamide known commonly as "nylon".

EXAMPLE 3–18

Effect of Different Nitrogenous Bases upon the Preparation of Oxime Product.

In order to establish the criticality that the pKa of the nitrogenous base plays upon the preparation of oxime, the following reductions of nitrotridecane were carried out using water-miscible amines having pKa's of about 5.25 to 11.25. One to two gram portions of silver nitrate catalyst (0.006 to 0.012 mole), and 18 ml portions of the designated amine base were used at the indicated temperatures and pressures. The reduction procedure described in Example I was followed. The success of the reductions were evaluated on a "go" or "no-go" basis, using gas liquid phase chromatography and infrared analysis of samples taken of the paraffinic phase at regular time intervals. If a significant uptake of nitroparaffin was detected, the paraffinic phase was removed by decantation after cooling, and the product worked-up by the techniques of Example 1. The data contained in Table 1 establishes that only bases having pKa in excess of 9.0 are useful and that the most useful bases are of the bidentate and multidentate type having a pKa between 9.0 and 11.5.

TABLE I

| EXAMPLE | SOLVENT | pKa* | SILVER ACETATE: SUBSTRATE MOLAR RATIO | AMINE: WATER WEIGHT RATIO | TEMP. (°C) | TIME (HRS) | NITRO TRIDECANE OXIME PRODUCED |
|---|---|---|---|---|---|---|---|
| 3 | Pyridine | 5.17 | 1:2 | 7:1 | 85 | 6 | No |
| 4 | N,N,N',N',-Tetramethyl-ethylenediamine | 5.85 | 1:2 | 7:1 | 85 | 6 | No |
| 5 | Triethanolamine | 7.77 | 1:2 | 7:1 | 85 | 6 | No |
| 6 | Morpholine | 8.36 | 1:2 | 7:1 | 80 | 6 | No |
| 7 | Ammonia | 9.21 | 1:1 | 3:7 | 60–80 | 6 | Yes |
| 8 | Diethanolamine | 9.35 | 1:1 | 7:1 | 85 | 6 | Yes |
| 9 | Tetraethylenepentamine | 9.9 | 1:2 | 7:1 | 85 | 6 | Yes |
| 10 | Triethylenetetramine | 9.92 | 1:2 | 7:1 | 85 | 6 | Yes |
| 11 | Ethylenediamine | 9.98 | 1:2 | 7:1 | 90 | 6 | Yes |
| 12 | n-Hexylamine | 10.40 | 1:1 | 7:1 | 85 | 6 | Yes |
| 13 | 1,3-diaminopropane | 10.54 | 1:1 | 7:1 | 85 | 6 | Yes |
| 14 | n-Butylamine | 10.59 | 1:1 | 7:1 | 75 | 6 | Yes |
| 15 | 3,3'-iminobispropylamine | 10.70 | 1:2 | 7:1 | 85 | 6 | Yes |
| 16 | 1,6-diaminohexane | 11.1 | 1:1 | 7:1 | 85 | 6 | Yes |
| 17 | Piperidine | 11.22 | 1:1 | 7:1 | 70 | 6 | Yes |
| 18 | Tetramethylguanidine | 11.50 | 1:2 | 7:1 | 80 | 6 | Yes |

*First Acid Dissociation Constant at 25°C in aqueous solution as reported in the literature, primarily from H. K. Hall, J. Am. Chem. Soc. 79, 5441 (1957) and "Stability Constants", Part I, Chem. Soc. Special Pub. No. 6.

EXAMPLES 19 TO 25

Effect of Variations of Pressure on the Reduction of Nitrated Substrates to the Oxime.

Using the procedure of Example 1, reduction of a one-part-by-weight portion of charge stock comprising 15 parts by weight of $C_{10}$–$C_{14}$ nitroparaffin (0.56 molar concentration), 82 parts by weight of $C_{10}$–$C_{14}$ n-paraffin (3.8 molar concentration) and 3 parts by weight of other oxygenates are run using a one-part-by-weight portion of catalyst solution composed of 10 parts by weight silver salt (0.5 molar concentration), 85 parts by weight of ethylenediamine (13 molar concentration) and 5 parts by weight of water (2.5 molar concentration). Reductions are carried out at 85°C. under an atmosphere of carbon monoxide at pressures ranging from 0–1000 psig. After 6 hours the mixtures are quenched and gas chromatographic analysis is used to determine the conversion to the desired oxime product. As can be seen by Table II (which follows), pressures below 100 psig substantially retard the conversion rate.

EXAMPLES 26–30

Effect of Varying Temperatures on the Reduction of Nitrated Substrates to the Oxime.

In these examples, the reduction of Example I is repeated at different temperature. Table III shows the results obtained. It should be noted that the best yields are obtained in the range 70° to 90°C.

TABLE II

| Example | Catalyst | Substrate | Solvent | Temp. (°C) | CO Pressure | Nitroparaffin Conversion (%) | Oxide Yield (%) |
|---|---|---|---|---|---|---|---|
| 19 | Silver Nitrate | $C_{10}$–$C_{14}$ Nitroparaffins | AQV. 90% EN" | 85 | ATM. | None | None |
| 20 | Silver Nitrate | $C_{10}$–$C_{14}$ Nitroparaffins | AQV. 90% EN" | 85 | 50 psig | 30 | 20 |
| 21 | Silver Acetate | $C_{10}$–$C_{14}$ Nitroparaffins | AQV. 90% EN" | 85 | 100 psig | 58 | 43 |
| 22 | Silver Acetate | $C_{10}$–$C_{14}$ Nitroparaffins | AQV. 90% EN" | 85 | 300 psig | 68 | 79 |
| 23 | Silver Acetate | $C_{10}$–$C_{14}$ Nitroparaffins | AQV. 90% EN" | 85 | 500 psig | 73 | 56 |
| 24 | Silver Nitrate | $C_{10}$–$C_{14}$ Nitroparaffins | AQV. 90% EN" | 85 | 800 psig | 70 | 50 |
| 25 | Silver Nitrate | $C_{10}$–$C_{14}$ Nitroparaffins | AQV. 90% EN" | 85 | 1000 psig | 64 | 40 |

"EN = ethylenediamine

TABLE III

| Example | Silver Salt Conc. (%W/V) | Silver Salt: Nitroparaffin Ratio | Solvent Composition | Temp. (°C) | CO Pressure (psig) | Time (Hrs) | % Conversion of Nitroparaffin to Oxime |
|---|---|---|---|---|---|---|---|
| 26 | 5.2 | 2:3 | AQV. 90% Ethylenediamine | 40 | 1000 | 8 | None |
| 27 | 5.2 | 2:3 | AQV. 90% Ethylenediamine | 60 | 1000 | 8 | 22 |
| 28 | 5.2 | 2:3 | AQV. 90% Ethylenediamine | 70 | 1000 | 8 | 52 |
| 29 | 4.9 | 1:1 | AQV. 90% Ethylenediamine | 90 | 500 | 4 | 78 |
| 30 | 6.7 | 2:3 | AQV. 90% Ethylenediamine | 120 | 1000 | 8 | 40 |

EXAMPLES 31–38

Effect of Varying the Proportion of the Components of the Catalyst Solution on Conversions of Nitroparaffin Substrate to the Oxime.

Using the apparatus and preparative techniques described in Example 1, a pure $C_{10}$–$C_{14}$ mixture of nitroparaffin substrate is reduced at 85°C and 500 psig of carbon monoxide using varying molar ratios of silver acetate, ethylenediamine, water and nitroparaffin substrate. Infrared, nuclear magnetic resonance and gas chromatography are used to establish that the desired oxime has been produced. Table IV which follows shows that variations in the molar proportions of ethylenediamine to nitroparaffin to silver catalyst in some instances have a substantial effect upon the conversion of nitroparaffin to oxime.

TABLE IV

| Example | Silver Acetate Conc. (%W/V) | Silver Acetate: Nitroparaffin Ratio | Solvent Composition | Temp. (°C) | CO Pressure (psig) | Time (Hrs) | % Conversion of Nitroparaffin to Oxime |
|---|---|---|---|---|---|---|---|
| 31 | 0.5 | 1:10 | AQV. 90% Ethylenediamine | 85 | 500 | 6 | 44 |
| 32 | 1.2 | 1:4 | AQV. 90% Ethylenediamine | 85 | 500 | 6 | 38 |
| 33 | 4.9 | 1:1 | AQV. 90% Ethylenediamine | 85 | 500 | 6 | 77 |
| 34 | 9.8 | 2:1 | AQV. 90% Ethylenediamine | 85 | 500 | 6 | 92 |
| 35 | 2.5 | 1:2 | AQV. 30% Ethylenediamine | 85 | 500 | 6 | 5 |
| 36 | 2.5 | 1:2 | AQV. 50% Ethylenediamine | 85 | 500 | 6 | 26 |
| 37 | 2.5 | 1:2 | AQV. 80% Ethylenediamine | 85 | 500 | 6 | 70 |
| 38 | 2.5 | 1:2 | Pure Ethylenediamine | 85 | 500 | 6 | 78 |

EXAMPLES 39–44

Reduction of Other Nitroparaffins.

Using the quantities of the silver salt catalyst, ethylenediamine and water and substrate indicated, and the procedure of Example 1, various nitroparaffinic substrates containing 3 to 20 carbon atoms are selectively reduced to the corresponding oxime at the pressures of CO and temperatures shown with a molar ratio of nitroparaffin to catalyst of about 1:1. In each instance the reduction is run for 4 to 8 hours. Again, infrared, nuclear magnetic resonance and standard samples are used to confirm the identity of the oxime product. The results appear in Table IV.

TABLE V

| Example | Silver Catalyst Composition | Conc. (%) | Nitroparaffin Substrate | Solvent Composition | Temp. (°C) | CO Pressure (psig) | Substrate Conv. (%) | Oxime Yield (%) |
|---|---|---|---|---|---|---|---|---|
| 39 | AgNO₃ | 5.1 | 15% $C_{10}$–$C_{14}$ Nitroparaffin 85% $C_{10}$–$C_{14}$ Paraffin | AQV. 90% En AQV. 90% EN | 95 85 | 1000 500 | 64 73 | 48 56 |
| 40 | AgOAc | 4.9 | $C_{10}$–$C_{14}$ Nitroparaffins | AQV. 90% EN | 85 | 100 | 100 | 53 |
| 41 | AgOAc | 6.6 | Nitrocyclohexane | AQV. 90% EN | 85 | 100 | 100 | 53 |
| 42 | AgOAc | 6.6 | Nitrocyclohexane | AQV. 90% EN | 85 | 100 | 100 | 53 |
| 43 | AgOAc | 5.0 | Nitropropane | AQV. 90% EN | 85 | 500 | N.D.* | 5 |
| 44 | AgNO₃ | 5.1 | 25% $C_{16}$–$C_{20}$ Nitroparaffin 75% $C_{16}$–$C_{20}$ Paraffin | AQV. 90% EN | 85 | 500 | 30 | 25 |

*N.D. = not determined

EXAMPLES 45–55

Comparisons of the Catalytic Activity of the Silver Salt Catalyst with Other Cationic Catalysts.

Using the apparatus and experimental techniques of Example 1, the following metal salt catalysts which are usually considered similar in catalytic activity to silver salts are evaluated in a side-by-side comparison with silver acetate in reducing nitroparaffin to the corresponding oxime. The reaction conditions are listed below. Table VI establishes that mercury (II), cobalt (II), manganese, iron, chromium and gold are inactive in the reduction of linear nitroparaffin substrates to the corresponding oxime under reaction conditions in which silver salts function well.

TABLE VI

| Example | Catalyst | Substrate | Solvent | Temp. (°C) | CO Pressure | Nitroparaffin Conversion (%) | Products |
|---|---|---|---|---|---|---|---|
| 45 | HgCl₂ | Nitrotridecane | AQV. 90% EN | 85 | 1 ATM | None | None |
| 46 | HgCl₂ | $C_{10}$–$C_{14}$ Nitroparaffins | AQV. 90% EN | 95 | 1000 psig | None | None |
| 47 | AgNO₃ | $C_{10}$–$C_{14}$ Nitroparaffins | AQV. 90% EN | 95 | 1000 psig | 64 | Paraffin Oximes |
| 48 | HAuCl₃ | $C_{10}$–$C_{14}$ Nitroparaffins | AQV. 90% EN | 95 | 1 ATM 1000 psig | None | None |
| 49 | CrCl₃ | Nitrotridecane | AQV. 90% EN | 84 | 1 ATM | None | None |

TABLE VI-continued

| Example | Catalyst | Substrate | Solvent | Temp. (°C) | CO Pressure | Nitroparaffin Conversion (%) | Products |
|---|---|---|---|---|---|---|---|
| 50 | CoCl$_2$ | Nitrotridecane | AQV. 75% EN | 84 | 1 ATM | None | None |
| 51 | CoCl$_2$ | C$_{10}$-C$_{14}$ Nitroparaffins | AQV. 80% EN | 100 | 1000 psig | None | None |
| 52 | Ni(OAc)$_2$ | Nitrododecane | AQV. 75% EN | 85 | 700 psig | None | None |
| 53 | FeCl$_2$ | Nitrotridecane | AQV. 90% EN | 85 | 1 ATM | None | None |
| 54 | FeCl$_2$ | Nitrotridecane | AQV. 90% EN | 85 | 1000 psig | None | None |
| 55 | MnCl$_2$ | Nitrotridecane | AQV. 90% EN | 85 | 1000 psig | None | None |

As can be seen by the results presented in Table VI, mercury (II), cobalt (II) manganese and nickel (II) were found to be inactive under reaction conditions where silver salt catalysts function effectively. Other metal salts such as iron, chromium and gold were also inactive.

The preceding specification, including the numerous embodiments and examples establish that the reductive process is not only advantageous but produces unexpected results. For instance, not only are yields of oxime good but the reduction proceeds relatively rapidly to produce oxime substantially free from the fully reduced, undesired amine contaminants. In addition, the reaction can be operated at relatively moderate conditions of temperature and pressure using standard hydrogenation equipment and techniques.

The results obtained in the practice of this invention are rather surprising in that silver salt catalysts have been found to demonstrate relatively good catalytic activity under reaction conditions which fail to produce catalytic activity in related cations. That is, mercury (II), cobalt (II) manganese and nickel (II) which are also known[1] to activate molecular carbon monoxide are inactive as reduction catalysts under reaction conditions sufficient to activate silver. Similarly, other metals such as iron, chromium, and gold were also inactive.

[1] J. J. Byerley and E. Peters, Canadian Journal of Chemistry, 47, 313 (1969) and references therein.

While the rates of reactants, temperatures and pressures are critical in the inventive process, in other respects the process is flexible. That is, the substrates, the type of silver salt and the choice of nitrogenous base can be varied.

The metes and bounds of this invention are best determined by the claims which follow, read in conjunction with the preceding specification.

What is claimed is:

1. A process for reducing mixtures of mono-nitrated paraffin substrates containing 3 to 40 carbon atoms, to the corresponding paraffinone oxime products without producing substantial quantities of the fully reduced paraffinic amines, consisting essentially of:
  a. forming a homogenous reaction mixture of the following components in the proportions indicated:
    1. a molar equivalent of said mono-nitroparaffins to be reduced,
    2. from about 1 to 100 molar equivalents of a water-miscible nitrogenous base selected from the group consisting of monodentate amines, bidentate amines and multidentate amines, said base having a pKa strength between about 9.5 to 11.5, and being capable of solubilizing or chelating silver salts,
    3. from about 0.1 to 2 molar equivalents of silver salt said silver salt being selected from the group consisting of silver salts of mineral acids and silver salts of organic acids, said silver salts being soluble in said nitrogenous base, and
    4. from 0 to 100 molar equivalents of water;
  b. heating said reaction mixture at temperatures ranging from about 40° to 120°C, in the presence of a carbon monoxide atmosphere, at superatmospheric pressures ranging from about 300 psig to 1000 psig, until substantially all of the said monoparaffins are reduced to the corresponding paraffinone oxime products, and
  c. isolating the paraffinone oximes contained therein.

2. The process of claim 1 wherein the nitroparaffin substrates are mixtures of linear nitroparaffins containing from 10 to 20 carbon atoms and the nitrogenous base is ethylenediamine.

3. The process of claim 2 wherein the nitroparaffin substrate contains paraffinic solvent.

4. The process of claim 2 wherein the catalyst system is aqueous.

5. The process of claim 2 wherein the catalyst system is non-aqueous.

6. A process for preparing paraffinone oximes from mono-nitroparaffin substrates selected from the group consisting of linear nitroparaffins containing 10 to 15 carbon atoms, mixtures of said linear nitroparaffins and mixtures of nitrocycloparaffins, comprising the steps of:
  a. forming a homogenous reaction mixture containing the following components in the proportions indicated:
    1. 1 molar equivalent of the C$_{10}$-C$_{15}$ nitroparaffins to be reduced,
    2. from about 1 to 20 molar equivalents of nitrogenous base selected from bidentate amines and multidentate amines having a pKa strength from about 9 to 11.5, said nitrogenous base being selected from the group consisting of ethylenediamine, triethylenetetramine, tetraethylenepentamine, and 3,3-iminobis propylamine,
    3. from about 0 to 10 molar equivalents of water,
    4. from about 0.1 to 2 molar equivalents of silver salt being selected from the group consisting of silver acetate, silver formate, silver tartrate and silver citrate, and
  b. heating said reaction mixture at temperatures ranging from about 70° to 90°C, in the presence of a carbon monoxide atmosphere, at superatmospheric pressures ranging from about 300 psig to 1000 psig, until substantial conversion of said mon-nitroparaffin substrates to their corresponding paraffinone oxime takes place, and
  c. isolating said paraffinone oximes contained therein.

7. The process of claim 6 wherein the nitroparaffin substrate is a nitrocycloparaffin.

8. The process of claim 7 wherein the nitrocycloparaffin is nitrocyclohexane.

9. The process of claim 6 wherein the nitroparaffin substrate contains paraffinic solvent.

10. A process for reducing mono-nitroparaffin substrates containing 10 to 15 carbon atoms to the corresponding paraffinone oxime products without producing substantial quantities of the fully reduced paraffinic amines, consisting essentially of:
   a. admixing each molar equivalent of mono-nitroparaffinic substrate selected from the group consisting of nitrocyclohexane, single linear nitroparaffins containing between 10 and 15 carbon atoms and mixtures of linear nitroparaffins containing between 10 and 15 carbon atoms with a catalyst system of:
      1. from about 1 to 20 molar equivalents of water-miscible nitrogenous base selected from the group consisting of bidentate amines and multidentate amines having a pKa between 9 and 11.5,
      2. from about 0.1 to 2.0 molar equivalents of silver salt soluble in said nitrogenous base, said silver salt being selected from the group consisting of silver salts of mineral acids, silver salts of monocarboxylic acids, silver salts of dicarboxylic acids and silver salts of tricarboxylic acids, and
      3. from about 0 to 10 molar equivalents of water to form a homogenous reaction mixture,
   b. heating said reaction mixture at temperatures between 70° and 90°C, at superatmospheric pressures ranging from about 300 psig to 1000 psig, in a carbon monoxide atmosphere, until substantial conversion of said substrates to their corresponding oximes is obtained, and
   4. isolating said oximes contained therein.

11. A process for preparing paraffinone oximes from mono-nitroparaffin substrates selected from the group consisting of linear nitroparaffins containing 10 to 15 carbon atoms, nitrocycloparaffins containing 10 to 15 carbon atoms, mixtures of said linear nitroparaffins and mixtures of nitrocycloparaffins, by the steps of:
   a. forming a homogenous reaction mixture containing the following components in the proportions indicated:
      1. 1 molar equivalent of the $C_{10}$–$C_{15}$ nitroparaffins to be reduced,
      2. from about 1 to 20 molar equivalents of ethylenediamine,
      3. from about 0 to 10 molar equivalents of water,
      4. from about 0.1 to 2 molar equivalents of a silver salt selected from the group consisting of silver acetate, silver nitrate and mixtures thereof,
   b. heating said reaction mixture at temperatures ranging from about 70° to 90°C, in the presence of a carbon monoxide atmosphere, at superatmospheric pressures ranging from about 300 psig to 1000 psig, until substantial conversion of said mono-nitroparaffin substrates to their corresponding paraffinone oxime takes place, and
   c. isolating said paraffinone oximes contained therein.

* * * * *